United States Patent
Rao et al.

(10) Patent No.: US 9,180,297 B2
(45) Date of Patent: Nov. 10, 2015

(54) SYSTEM AND METHOD FOR SPINAL CORD MODULATION TO TREAT MOTOR DISORDER WITHOUT PARESTHESIA

(71) Applicant: BOSTON SCIENTIFIC NEUROMODULATION CORPORATION, Valencia, CA (US)

(72) Inventors: Prakash Rao, Philadelphia, PA (US); Anita Yip, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/199,152

(22) Filed: Mar. 6, 2014

(65) Prior Publication Data
US 2014/0343655 A1  Nov. 20, 2014

Related U.S. Application Data

(60) Provisional application No. 61/824,230, filed on May 16, 2013.

(51) Int. Cl.
*A61N 1/00* (2006.01)
*A61N 1/36* (2006.01)
*A61N 1/05* (2006.01)

(52) U.S. Cl.
CPC ........ *A61N 1/36067* (2013.01); *A61N 1/36171* (2013.01); *A61N 1/36175* (2013.01); *A61N 1/0551* (2013.01)

(58) Field of Classification Search
CPC ............ A61N 1/36067; A61N 1/3605; A61N 1/3606; A61N 1/36064; A61N 1/36128; A61N 1/36135; A61N 1/36153; A61N 1/36157; A61N 1/36171; A61N 1/36175; A61N 1/36132; A61N 1/0551
See application file for complete search history.

(56) References Cited

U.S. PATENT DOCUMENTS

| | | |
|---|---|---|
| 6,516,227 B1 | 2/2003 | Meadows et al. |
| 6,675,046 B2 | 1/2004 | Holsheimer |
| 6,845,267 B2 | 1/2005 | Harrison et al. |
| 6,895,280 B2 | 5/2005 | Meadows et al. |

(Continued)

FOREIGN PATENT DOCUMENTS

| | | |
|---|---|---|
| WO | WO-2006029257 A2 | 3/2006 |
| WO | WO-2006135791 A2 | 12/2006 |

OTHER PUBLICATIONS

Morgante, L. et al., How many parkinsonian patients are suitable candidates for deep brain stimulation of subthalamic nucleus. Results of a questionnaire, Parkinsonism Relat Disord. 2007; 13:528-531.

(Continued)

*Primary Examiner* — George Manuel
(74) *Attorney, Agent, or Firm* — Schwegman Lundberg & Woessner, P.A.

(57) ABSTRACT

A method for of performing a medical procedure on a patient suffering from a movement disorder. The method comprises delivering electrical current having a defined pulse rate equal to or greater than 1500 Hz and/or a defined pulse duration equal to or less than 200 μs to spinal cord tissue of the patient in a manner that modulates neuronal traffic in at least one dorsal column (DC) nerve fiber of the patient, thereby treating symptoms of the movement disorder without causing the patient to perceive paresthesia from the delivered electrical current.

27 Claims, 5 Drawing Sheets

(56) References Cited

U.S. PATENT DOCUMENTS

| | | | |
|---|---|---|---|
| 6,950,707 B2 | 9/2005 | Whitehurst | |
| 6,993,384 B2 | 1/2006 | Bradley et al. | |
| 7,317,948 B1 | 1/2008 | King et al. | |
| 7,333,857 B2 | 2/2008 | Campbell | |
| 7,539,538 B2 | 5/2009 | Parramon et al. | |
| 7,650,184 B2 | 1/2010 | Walter | |
| 7,979,133 B2 | 7/2011 | Feler et al. | |
| 8,019,439 B2 | 9/2011 | Kuzma et al. | |
| 8,065,013 B2 * | 11/2011 | Bradley et al. | 607/46 |
| 8,170,675 B2 | 5/2012 | Alataris et al. | |
| 8,209,021 B2 | 6/2012 | Alataris et al. | |
| 8,224,453 B2 | 7/2012 | De Ridder | |
| 8,255,057 B2 | 8/2012 | Fang et al. | |
| 8,355,797 B2 | 1/2013 | Caparso et al. | |
| 8,359,102 B2 | 1/2013 | Alataris et al. | |
| 8,359,103 B2 | 1/2013 | Alataris et al. | |
| 8,380,318 B2 | 2/2013 | Kishawi et al. | |
| 8,396,559 B2 | 3/2013 | Alataris et al. | |
| 8,423,147 B2 | 4/2013 | Alataris et al. | |
| 8,455,716 B2 | 6/2013 | Huang et al. | |
| 8,504,147 B2 | 8/2013 | Deem et al. | |
| 8,615,300 B2 | 12/2013 | Feler et al. | |
| 8,649,874 B2 | 2/2014 | Alataris et al. | |
| 8,670,831 B2 | 3/2014 | Wacnik et al. | |
| 8,676,329 B2 | 3/2014 | Wacnik et al. | |
| 8,676,331 B2 | 3/2014 | Parker | |
| 8,731,675 B2 | 5/2014 | Ranu et al. | |
| 8,751,009 B2 | 6/2014 | Wacnik | |
| 9,002,459 B2 | 4/2015 | Lee et al. | |
| 2003/0139781 A1 | 7/2003 | Bradley et al. | |
| 2007/0060954 A1 | 3/2007 | Cameron et al. | |
| 2007/0150036 A1 | 6/2007 | Anderson | |
| 2007/0168004 A1 | 7/2007 | Walter | |
| 2007/0168007 A1 | 7/2007 | Kuzma et al. | |
| 2008/0188909 A1 | 8/2008 | Bradley | |
| 2009/0204173 A1 | 8/2009 | Fang et al. | |
| 2010/0010566 A1 | 1/2010 | Thacker et al. | |
| 2010/0023103 A1 | 1/2010 | Elborno | |
| 2010/0121409 A1 | 5/2010 | Kothandaraman et al. | |
| 2010/0249875 A1 | 9/2010 | Kishawi et al. | |
| 2010/0274312 A1 | 10/2010 | Alataris et al. | |
| 2010/0274314 A1 | 10/2010 | Alataris et al. | |
| 2010/0274315 A1 | 10/2010 | Alataris et al. | |
| 2010/0274317 A1 | 10/2010 | Parker et al. | |
| 2010/0274318 A1 | 10/2010 | Walker et al. | |
| 2010/0274326 A1 | 10/2010 | Chitre et al. | |
| 2011/0184488 A1 | 7/2011 | De Ridder | |
| 2012/0016437 A1 | 1/2012 | Alataris et al. | |
| 2012/0059446 A1 | 3/2012 | Wallace et al. | |
| 2012/0083709 A1 | 4/2012 | Parker et al. | |
| 2012/0203304 A1 | 8/2012 | Alataris et al. | |
| 2012/0253422 A1 | 10/2012 | Thacker et al. | |
| 2012/0265279 A1 | 10/2012 | Zhu et al. | |
| 2012/0283797 A1 | 11/2012 | De Ridder | |
| 2012/0290041 A1 | 11/2012 | Kim et al. | |
| 2012/0330391 A1 | 12/2012 | Bradley et al. | |
| 2013/0041425 A1 | 2/2013 | Fang et al. | |
| 2013/0066411 A1 | 3/2013 | Thacker et al. | |
| 2013/0116752 A1 | 5/2013 | Parker et al. | |
| 2013/0268021 A1 | 10/2013 | Moffitt | |
| 2013/0296975 A1 | 11/2013 | Lee et al. | |
| 2013/0310901 A1 * | 11/2013 | Perryman et al. | 607/72 |
| 2014/0081349 A1 | 3/2014 | Lee et al. | |

OTHER PUBLICATIONS

Thevathasan, W. et al., Spinal cord stimulation failed to relieve akinesia or restore locomotion in Parkinson disease. Neurology 210;74:1325-7.

Agari, T. et al., Spinal Cord Stimulation for the Treatment of Abnormal Posture and Gait Disorder in Patients with Parkinson's Disease, The 70th Annual Meeting Special Topis—Pat I: Validation and Prospects for Neuromodulation, Neural Med Chir (Tokyo) 52, 470-474, 2012.

Fenelon, G., Spinal Cord Stimulation for Chronic-Pain Improved Motor Function in a Patient with Parkinson's Disease, Parkinsonism and Related Disorders 18 (2012) 213-214.

Fuentes, R. et al., Restoration of Locomotive Function in Parkinson's Disease by Spinal Cord Stimulation: Mechanistic Approach, Eur J. Neurosci. Oct. 2010; 32(7): 1100-1108.

Fuentes, R. et al., Spinal Cord Stimulation Restores Locomotion in Animal Models of Parkinson's Disease, Mar. 20, 2009, vol. 323, pp. 1578-1582, Science, www.sciencemag.org.

Joseph, L. et al., High Frequency Stimulation Selectively Blocks Different Types of Fibers in Frog Sciatic Nerve, IEEE Trans Neural Syst Rehabil Eng. Oct. 2011; 19(5):550-557.

* cited by examiner

SYSTEM AND METHOD FOR SPINAL CORD MODULATION TO TREAT MOTOR DISORDER WITHOUT PARESTHESIA

RELATED APPLICATION DATA

The present application claims the benefit under 35 U.S.C. §119 to U.S. provisional patent application Ser. No. 61/824,230, filed May 16, 2013. The foregoing application is hereby incorporated by reference into the present application in its entirety.

FIELD OF THE INVENTION

The present inventions relate to systems and methods for treating motor disorders using spinal cord modulation.

BACKGROUND OF THE INVENTION

Parkinson's disease affects between 1.0-1.5 million Americans, which is greater than the number of patients diagnosed with multiple sclerosis, muscular dystrophy, and Lou Gehrig's disease combined. Each year, 50,000 American are diagnosed with Parkinson's disease. For some, the motor symptoms of Parkinson's disease are difficult to control even with dopaminergic treatments. Deep Brain Stimulation (DBS) has been applied therapeutically for well over a decade for the treatment of neurological disorders, including Parkinson's Disease, via electrical stimulation of one or more target sites, including the subthalamic nucleus (STN) and internal segment of globus pallidus (GPi). DBS has become a prominent treatment option for many disorders, because it is a safe, reversible alternative to lesioning. For example, DBS is the most frequently performed surgical disorder for the treatment of advanced Parkinson's disease. There have been approximately 30,000 patients world-wide that have undergone DBS surgery.

However, DBS needs a long, complex and invasive surgery to succeed. For example, multiple stimulation leads are typically implanted adjacent the target sites within the brain of the patient. In particular, multiple burr holes are cut through the patient's cranium as not to damage the brain tissue below, a large stereotactic targeting apparatus is mounted to the patient's cranium, and a cannula is scrupulously positioned through each burr hole one at a time towards each target site in the brain. Microelectrode recordings may typically be made to determine if each trajectory passes through the desired part of the brain, and if so, the stimulation leads are then introduced through the cannula, through the burr holes, and along the trajectories into the parenchyma of the brain, such that the electrodes located on the lead are strategically placed at the target sites in the brain of the patient. Disadvantageously, the cutting of multiple burr holes and the introduction of the leads along multiple trajectories into the brain increases trauma and risk to the patient. Additionally, the selection criteria restrict the patient population eligible for DBS to only 1.6-4.5% (see Morgante L., et al, How Many Parkinsonian Patients are Suitable Candidates for Deep Brain Stimulation of Subthalamic Nucleus. Results of a Questionaire, Parkinsonian Related Disorders, 2007; 13:528-531). Further details discussing the treatment of diseases using DBS are disclosed in U.S. Pat. Nos. 6,845,267 and 6,950,707, which are expressly incorporated herein by reference.

There is, thus, a need to develop less invasive efficacious treatments for patients with Parkinson's disease. Spinal Cord Stimulation (SCS) techniques, which is currently used in treating chronic neuropathic pain of the trunk and limbs by directly stimulating spinal cord tissue (e.g., the dorsal column) via one or more leads implanted within the epidural space, is a promising option for patients suffering from Parkinson's disease. It is believed that symptoms of motor disorders, such as Parkinson's disease, may be the result of control issues driven by sensory input. A patient with a motor disorder may have a healthy motor cortex, but the input to the motor cortex may be inappropriate. An imbalance between excitatory and inhibitory input into the motor cortex may result in motor disorder symptoms. Sensory input travels to the motor cortex via sensory nerves in the dorsal column. Thus, in an effort to restore balance between the excitatory and inhibitory inputs into the motor cortex, it is believe that stimulation applied to the dorsal column of the spinal cord in conventional SCS treatments may effectively treat motor disorders. Such dorsal column stimulation for treating symptoms of motor disorders has not yet found widespread use, however, because long-term efficacy in a large number of patients has not been demonstrated.

However, some have reported improvement of motor control using SCS in animal models and in humans. For example, using chronic and advanced Parkinson's disease rodent models, it has been shown that epidural electrical stimulation of the dorsal column was able to restore locomotive ability (see Romulo Fuentes, et al., Restoration of Locomotive Function in Parkinson's Disease by Spinal Cord Stimulation: Mechanistic Approach, Eur J Neurosci, 2010 October; 32(7): 1100-1108). A case study where SCS at the T9-T10 vertebral levels has been shown to alleviate motor Parkinsonian symptoms in the off-drug condition to the same extent as levodopa intake alone (see Fenelon G., Spinal Cord Stimulation for Chronic Pain Improved Motor Function in a Patient with Parkinson's Disease, Parkinsonian and Related Disorders 18 (2012) 213-214). Others have published that SCS can be used to treat movement disorders (see U.S. Patent Publications 2007/0060954, 2010/0023103, and 2012/0330391.

Thus, since SCS is a minimally-invasive approach, SCS techniques for effectively managing symptoms of motor disorders remain attractive in comparison to brain stimulation-based methods, such DBS. In order to achieve an effective result from conventional SCS, the stimulation lead or leads must be placed in a location, such that the delivered stimulation energy creates an electrical field, which when strong enough, depolarizes (or "stimulates") the neural fibers within the spinal cord beyond a threshold level, thereby inducing the firing of action potentials (APs) that propagate along the neural fibers to provide the desired efficacious therapy to the patient. It is believed that the antidromic activation (i.e., the APs propagate in a direction opposite to their normal direction, which in the case of the spinal cord dorsal column (DC) neural fibers, propagate in the caudal direction) of the large diameter DC neural fibers provides the actual pain relief to the patient by reducing/blocking transmission of smaller diameter pain fibers via interneuronal interaction in the dorsal horn of the spinal cord, while the orthodromic activation (i.e., the APs propagate in their normal direction, which in the case of the spinal cord, propagate in the rostral direction) of the large diameter DC neural fibers generate action potentials that arrive at the thalamus and are relayed to the sensory cortex, thereby creating a side-effect in the form of a sensation known as paresthesia, which can be characterized as a tingling sensation that replaces the pain signals sensed by the patient. The paresthesia induced by the stimulation and perceived by the patient should be located in approximately the same place in the patient's body afflicted by the motor disorder.

Although alternative or artifactual sensations are usually tolerated relative to the sensation of pain, patients sometimes report these sensations to be uncomfortable, and therefore, they can be considered an adverse side-effect to SCS therapy in some cases. There, thus, remains a need to treat movement disorders using SCS therapy while preventing patients from perceiving paresthesia.

SUMMARY OF THE INVENTION

In accordance with the present inventions, a method for of performing a medical procedure on a patient suffering from a movement disorder is provided. The method comprises delivering electrical current to spinal cord tissue of the patient in a manner that modulates neuronal traffic in at least one dorsal column (DC) nerve fiber of the patient, thereby treating symptoms of the movement disorder (e.g., Parkinson's disease, epilepsy, essential tremor, bradykinesia, akinesia, dystonia, multiple sclerosis, cerebral palsy, Guillain-Barre syndrome, Tourette's syndrome, spasms, and Wilson's disease) without causing the patient to perceive paresthesia from the delivered electrical current.

In one embodiment, the movement disorder affects a peripheral region of the patient, and the electrical current is delivered to the spinal cord tissue at a vertebral level (e.g., in the range of T1-T12) that corresponds to the peripheral region. The delivered electrical current may be a pulsed electrical current having a defined pulse rate (e.g., in the range of 1500 Hz to 50 KHz) and/or a defined pulse duration (e.g., in the range of 10 μs to 200 μs). The method may further comprise implanting at least one electrode in the epidural space of the patient, in which case, the electrical current is delivered by the electrode(s).

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
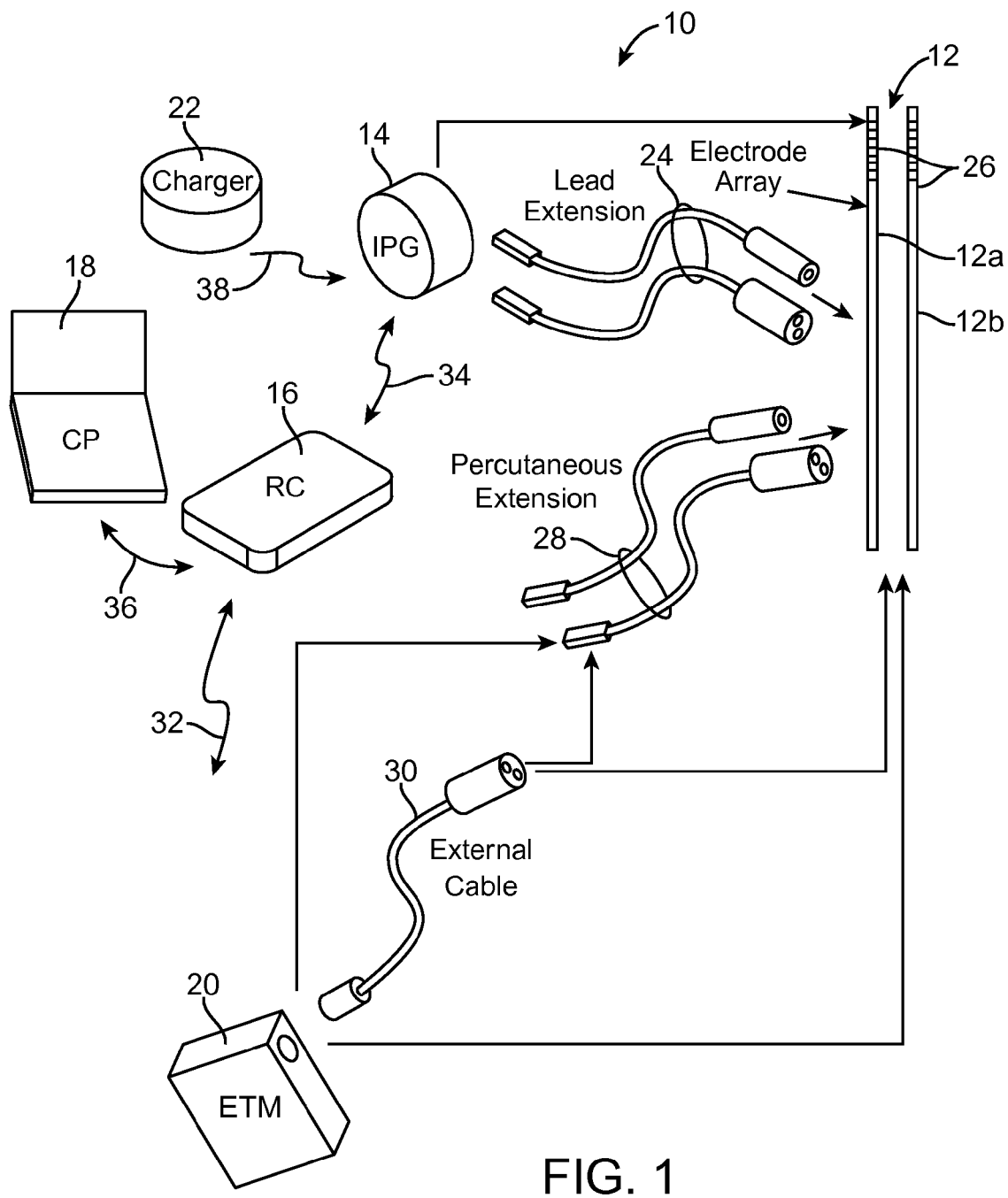
FIG. 1 is a plan view of a Spinal Cord Modulation (SCM) system constructed in accordance with one embodiment of the present inventions.

Turning first to FIG. 1, an exemplary SCM system 10 generally includes a plurality (in this case, two) of implantable neuromodulation leads 12, an implantable pulse generator (IPG) 14, an external remote controller RC 16, a clinician's programmer (CP) 18, an external trial modulator (ETM) 20, and an external charger 22.

The IPG 14 is physically connected via one or more percutaneous lead extensions 24 to the neuromodulation leads 12, which carry a plurality of electrodes 26 arranged in an array. In the illustrated embodiment, the neuromodulation leads 12 are percutaneous leads, and to this end, the electrodes 26 are arranged in-line along the neuromodulation leads 12. The number of neuromodulation leads 12 illustrated is two, although any suitable number of neuromodulation leads 12 can be provided, including only one. Alternatively, a surgical paddle lead in can be used in place of one or more of the percutaneous leads. As will be described in further detail below, the IPG 14 includes pulse generation circuitry that delivers electrical modulation energy in the form of a pulsed electrical waveform (i.e., a temporal series of electrical pulses) to the electrode array 26 in accordance with a set of modulation parameters.

The ETM 20 may also be physically connected via the percutaneous lead extensions 28 and external cable 30 to the neuromodulation leads 12. The ETM 20, which has similar pulse generation circuitry as the IPG 14, also delivers electrical modulation energy in the form of a pulse electrical waveform to the electrode array 26 accordance with a set of modulation parameters. The major difference between the ETM 20 and the IPG 14 is that the ETM 20 is a non-implantable device that is used on a trial basis after the neuromodulation leads 12 have been implanted and prior to implantation of the IPG 14, to test the responsiveness of the modulation that is to be provided. Thus, any functions described herein with respect to the IPG 14 can likewise be performed with respect to the ETM 20. For purposes of brevity, the details of the ETM 20 will not be described herein.

The RC 16 may be used to telemetrically control the ETM 20 via a bi-directional RF communications link 32. Once the IPG 14 and neuromodulation leads 12 are implanted, the RC 16 may be used to telemetrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14. As will be described in further detail below, the CP 18 provides clinician detailed modulation parameters for programming the IPG 14 and ETM 20 in the operating room and in follow-up sessions.

The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown). The clinician detailed modulation parameters provided by the CP 18 are also used to program the RC 16, so that the modulation parameters can be subsequently modified by operation of the RC 16 in a stand-alone mode (i.e., without the assistance of the CP 18).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present. For purposes of brevity, the details of the external charger 22 will not be described herein.

For purposes of brevity, the details of the RC 16, CP 18, ETM 20, and external charger 22 will not be described herein. Details of exemplary embodiments of these devices are disclosed in U.S. Pat. No. 6,895,280, which is expressly incorporated herein by reference.

Figure 2:
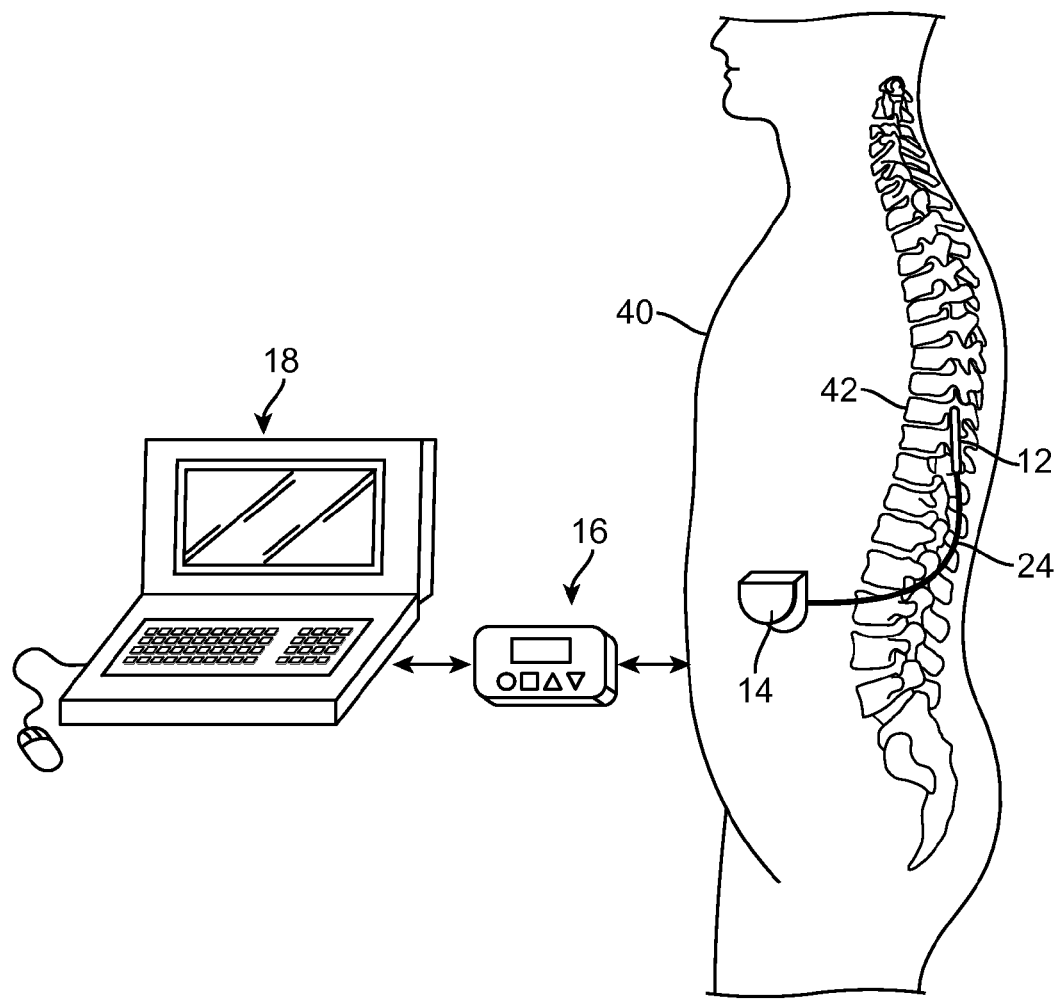
FIG. 2 is a plan view of the SCM system of FIG. 1 in use within a patient.

As shown in FIG. 2, the neuromodulation leads 12 are implanted within the spinal column 42 of a patient 40. The preferred placement of the neuromodulation leads 12 is adjacent, i.e., resting upon, the spinal cord area to be modulated. Due to the lack of space near the location where the neuromodulation leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neuromodulation leads 12. As there shown, the CP 18 communicates with the IPG 14 via the RC 16.

Figure 3:
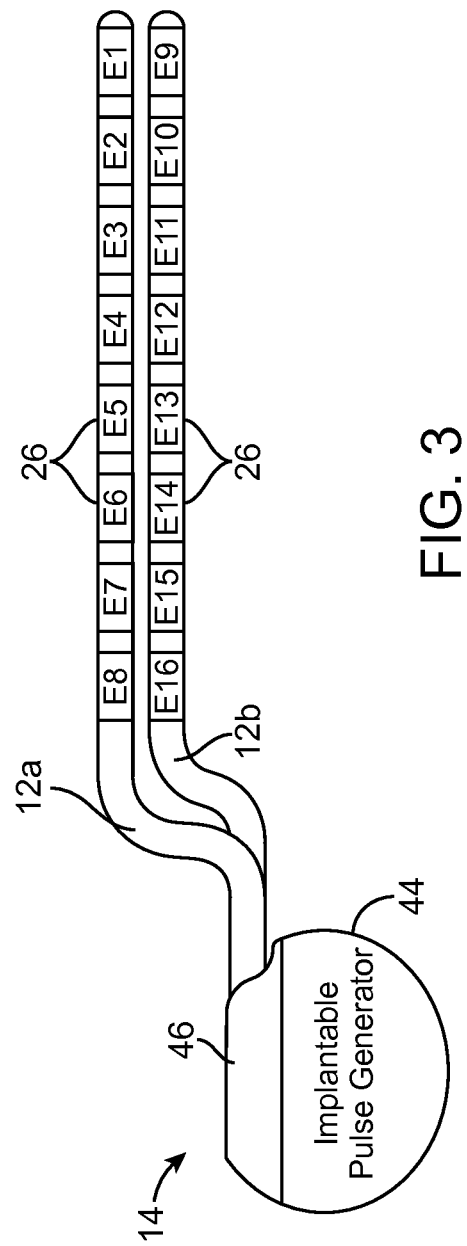
FIG. 3 is a plan view of an implantable pulse generator (IPG) and two percutaneous leads used in the SCM system of FIG. 1.

Referring now to FIG. 3, the external features of the neuromodulation leads 12 and the IPG 14 will be briefly described. One of the neuromodulation leads 12a has eight electrodes 26 (labeled E1-E8), and the other neuromodulation lead 12b has eight electrodes 26 (labeled E9-E16). The actual number and shape of leads and electrodes will, of course, vary according to the intended application. The IPG 14 comprises an outer case 44 for housing the electronic and other components (described in further detail below), and a connector 46 to which the proximal ends of the neuromodulation leads 12 mates in a manner that electrically couples the electrodes 26 to the electronics within the outer case 44. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

Figure 4:
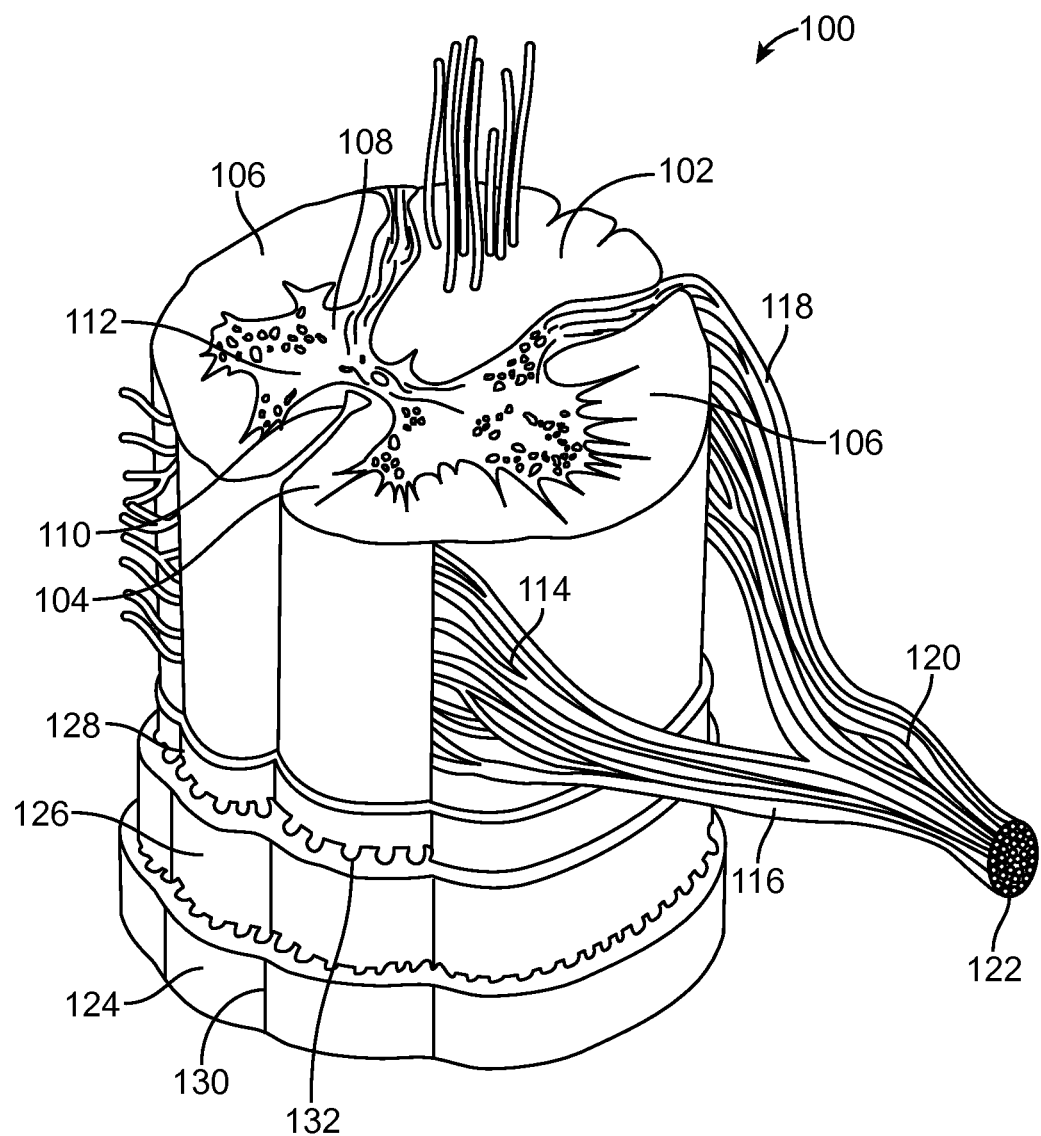
FIG. 4 is a perspective view of the spinal cord and spinal nerves.

Referring now to FIG. 4, the portions of the spinal cord 100 that are relevant to the present inventions will be described. The spinal cord 100 is divided into three functional columns: the dorsal column 102, the ventral column 104, and the lateral columns 106. Similarly, the butterfly-shaped gray matter of the spinal cord 100 is divided into the dorsal horn 108, the ventral horn 110, and the lateral horn 112.

A group of motor nerve rootlets (ventral root (VR) nerve fibers) 114 branch off of the ventral horn 110 and combine to form the ventral root 116. Similarly, a group of sensory nerve rootlets (dorsal root (DR) nerve fibers) 118 branch off of the dorsal horn 108 and combine to form the dorsal root 120. The dorsal root 120 and the ventral root 116 combine to form the spinal nerve 122, which innervates peripheral regions (e.g., arms, legs, etc.) of the patient's body. A number of spinal nerves branch off the spinal cord. In each patient, there are eight cervical spinal nerves designated C1-C8, twelve thoracic spinal nerves designated T1-T12, five lumbar spinal nerves designated L1-L5, and five sacral spinal nerves designated S1-S5. The spinal cord 100 is protected by three layers of connective tissue, the dura mater 124, the arachnoid 126, and the pia mater 128, collectively referred to as meninges. An epidural space 130 surrounds the dura mater 124, and a subarachnoid space 132 lies under the arachnoid 126. The epidural space 130 may be topologically divided into two halves: a ventral epidural space 130a and a dorsal epidural space 130b (shown in FIG. 5).

Having the structure and function of the SCM system 10 and the relevant anatomy, one method of using the SCM system 10 to treat a motor disorder suffered by a patient will now be described. In the illustrated method, the motor disorder is Parkinson's disease, although other types of motor disorders, such as epilepsy, essential tremor, bradykinesia, akinesia, dystonia, multiple sclerosis, cerebral palsy, Guillain-Barre syndrome, Tourette's syndrome, spasms, and Wilson's disease, may be treated.

Figure 5:
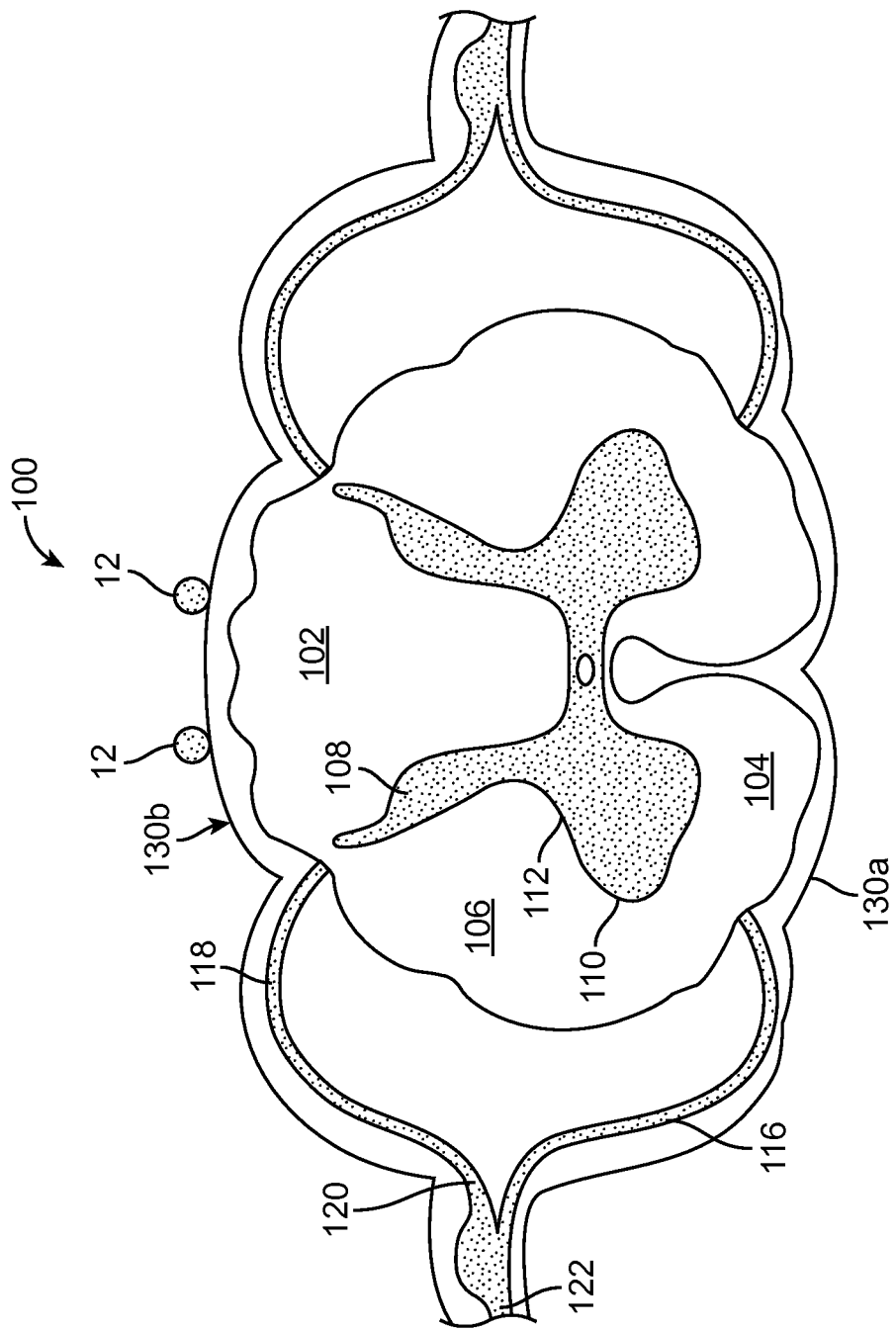
FIG. 5 is a cross-sectional view of the spinal cord showing an electrode arrangement relative to the spinal cord in accordance with a modulation regimen of the present inventions.

To this end, the leads 12 are positioned in the dorsal epidural space 130b, as shown in FIG. 5. With the leads 12 positioned in the dorsal epidural space 130b, electrical current delivered by the electrodes 26 on the leads 12 is applied to the dorsal column 102. The magnitude of the electrical current is such that the neuronal traffic in at least one affected dorsal column nerve fiber innervating the peripheral region of the patient's body that exhibits the symptoms of the motor disorder is modulated. To this end, the electrical current is preferably delivered to the dorsal column 102 at a vertebral level that corresponds to the peripheral region of the patient affected by the movement disorder. For example, the electrical current may be delivered to a vertebral level in the range of T1-T12, and more particularly, in the range of T9-T10.

Significantly, the electrical current delivered to the dorsal column 102 has a defined pulse rate and/or defined pulse duration that does not cause the patient to perceive paresthesia as a result of the delivered electrical current. For example, the delivered electrical current may take the form of an electrical pulse train at a relatively low pulse amplitude (e.g., 2.5 ma), a relatively high pulse rate (e.g., in the range of 1500 Hz-50 KHz, preferably equal to or greater than 2500 Hz), and a relatively low pulse width (e.g., in the range of 10 μs-200 μs, preferably equal to or less than 100 μs, and more preferably equal to or less than 50 μs). Preferably, the electrical pulse train has at least an anodic phase (whether a pure monophasic anodic pulse train, a biphasic pulse train with an active cathodic charge recovery phase, or a biphasic pulse train with a passive charge recovery phase), which is believed to provide sub-threshold therapy more effectively than a cathodic phase.

The electrodes 26 on the leads 12 are preferably narrowly-spaced, although widely spaced electrodes may be utilized. Although the electrodes 26 on the leads 12 are non-directional, radially segmented electrodes 26 may alternatively be used to provide directionality to the electrical current delivery. Insulated electrodes for capacitively (non-charge transferring) electrodes can alternatively be used. Different types of simple or complex electrical pulse trains may be employed; for example, subthreshold, hyperpolarizing, anodic pre-pulsing (conditioning), continuous or burse modulation (to hyperpolarize neurons closest to the active electrode(s)), sinusoidal, rectangular, triangular, exponential, trapezoidal, sawtooth, or spiked charge balanced, symmetrical or asymmetrical pulse complexes, etc.). The leads 12 may be implanted either permanently or on a temporary basis. The SCM system 10 may be used as a successful adjunct to other implantable medical devices; for example, pacemakers, defibrillators, deep brain stimulators, vagal nerve stimulators, SCM with leads placed in other spinal locations, peripheral nerve field stimulators with leads 12 placed in other areas in the periphery, etc.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method for performing a medical procedure on a patient suffering from a movement disorder, comprising:
   delivering electrical current to spinal cord tissue of the patient in a manner that modulates neuronal traffic in at least one dorsal column (DC) nerve fiber of the patient, thereby treating symptoms of the movement disorder without causing the patient to perceive paresthesia from the delivered electrical current.

2. The method of claim 1, wherein the movement disorder is Parkinson's disease.

3. The method of claim 1, wherein the movement disorder is one of epilepsy, essential tremor, bradykinesia, akinesia, dystonia, multiple sclerosis, cerebral palsy, Guillain-Barre syndrome, Tourette's syndrome, spasms, and Wilson's disease.

4. The method of claim 1, wherein the movement disorder affects a peripheral region of the patient, and the electrical current is delivered to the spinal cord tissue at a vertebral level that corresponds to the peripheral region.

5. The method of claim 1, wherein the electrical current is delivered to the spinal cord tissue at a vertebral level in the range of T1-T12.

6. The method of claim 1, wherein the electrical current is delivered to the spinal cord tissue at a vertebral level in the range of T9-T10.

7. The method of claim 1, wherein the delivered electrical current is a pulsed electrical current having a defined pulse rate and a defined pulse width.

8. The method of claim 7, wherein the defined pulse rate is equal to or greater than 1500 Hz.

9. The method of claim 7, wherein the defined pulse rate is equal to or greater than 2500 Hz.

10. The method of claim 7, wherein the defined pulse rate is in the range of 1500 Hz to 50 KHz.

11. The method of claim 7, wherein the defined pulse width is equal to or less than 200 μs.

12. The method of claim 7, wherein the defined pulse width is equal to or less than 100 μs.

13. The method of claim 7, wherein the defined pulse width is equal to or less than 50 μs.

14. The method of claim 1, further comprising implanting at least one electrode in the epidural space of the patient, wherein the electrical current is delivered by the at least one electrode.

15. A method for performing a medical procedure on a patient suffering from a movement disorder, comprising:
   delivering pulsed electrical current having a defined pulse rate equal to or greater than 1500 Hz, or having a defined pulse duration equal to or less than 200 μs, or having both the defined pulse rate equal to or greater than 1500 Hz and the defined pulse duration equal to or less than 200 μs to spinal cord tissue of the patient in a manner that modulates neuronal traffic in at least one dorsal column (DC) nerve fiber of the patient, thereby treating symptoms of the movement disorder.

16. The method of claim 15, wherein the movement disorder is Parkinson's disease.

17. The method of claim 15, wherein the movement disorder is one of epilepsy, essential tremor, bradykinesia, akinesia, dystonia, multiple sclerosis, cerebral palsy, Guillain-Barre syndrome, Tourette's syndrome, spasms, and Wilson's disease.

18. The method of claim 15, wherein the movement disorder affects a peripheral region of the patient, and the electrical current is delivered to the spinal cord tissue at a vertebral level that corresponds to the peripheral region.

19. The method of claim 15, wherein the electrical current is delivered to the spinal cord tissue at a vertebral level in the range of T1-T12.

20. The method of claim 15, wherein the electrical current is delivered to the spinal cord tissue at a vertebral level in the range of T9-T10.

21. The method of claim 15, wherein the delivered electrical current has a defined pulse rate equal to or greater than 1500 Hz.

22. The method of claim 21, wherein the defined pulse rate is equal to or greater than 2500 Hz.

23. The method of claim 21, wherein the defined pulse rate is in the range of 1500 Hz to 50 KHz.

24. The method of claim 15, wherein the delivered electrical current has a defined pulse duration equal to or less than 200 μs.

25. The method of claim 24, wherein the defined pulse width is equal to or less than 100 μs.

26. The method of claim 24, wherein the defined pulse width is equal to or less than 50 μs.

27. The method of claim 15, further comprising implanting at least one electrode in the epidural space of the patient, wherein the electrical current is delivered by the at least one electrode.

* * * * *